(12) United States Patent
Cheng et al.

(10) Patent No.: US 9,133,512 B2
(45) Date of Patent: Sep. 15, 2015

(54) SYSTEM FOR DETERMINING AMINO ACID SEQUENCE OF POLYPEPTIDE

(71) Applicant: Chung Yuan Christian University, Tao-Yuan (TW)

(72) Inventors: Chean-Yeh Cheng, Tao-Yuan (TW); Li-Te Yu, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 12 days.

(21) Appl. No.: 13/850,239

(22) Filed: Mar. 25, 2013

(65) Prior Publication Data
US 2014/0170759 A1    Jun. 19, 2014

(30) Foreign Application Priority Data
Dec. 18, 2012 (TW) .............................. 101148182 A

(51) Int. Cl.
*C12Q 1/68* (2006.01)
*G01N 33/68* (2006.01)

(52) U.S. Cl.
CPC .......... *C12Q 1/6872* (2013.01); *G01N 33/6806* (2013.01); *G01N 33/6848* (2013.01); *Y10T 436/143333* (2015.01)

(58) Field of Classification Search
CPC .................... C12Q 1/6872; Y10T 436/143333
USPC ..................... 436/130, 94; 428/514; 204/409; 422/68.1
See application file for complete search history.

(56) References Cited

U.S. PATENT DOCUMENTS

2010/0284918 A1*   11/2010   Rohlff ............................ 424/9.1

OTHER PUBLICATIONS

Cheng et al. "Simultaneous analysis of aspartame and its hydrolysis products of Coca-Cola Zero by on-line postcolumn derivation fluorescence detection and ultraviolet detection coupled two-dimensional high-performance liquid chromatography" Journal of Chromatography A, 1218 (2011), pp. 2976-2983.

* cited by examiner

*Primary Examiner* — Rebecca M Fritchman
(74) *Attorney, Agent, or Firm* — Donald E. Stout; Stout, Uxa & Buyan, LLP

(57) ABSTRACT

This invention discloses systems and methods for determining the sequence of amino acids in a short peptide chain that constructs a protein. The protein is firstly hydrolyzed to various short peptides and amino acid enantiomers. Then, the systems and method are used to separate the short peptides and the amino acid enantiomers, identify qualitatively each of the amino acid enantiomers, and obtain the molecular mass signal for each of the peptides. After that, the identified amino acid enantiomers are used to construct any possible short peptides in an order from the smallest molecular weight dipeptide to higher molecular weight short peptides, and the correct short peptides is confirmed by matching the molecular weight obtained from the mass spectrometry measurement, then, the short peptides are combined to give a large peptide. The process is continued until the whole amino acid sequence of the peptide chain of protein can be determined.

5 Claims, 9 Drawing Sheets

SYSTEM FOR DETERMINING AMINO ACID SEQUENCE OF POLYPEPTIDE

CROSS-REFERENCE TO RELATED APPLICATIONS

This application claims priority to Taiwan Patent Application No. 101148182, filed Dec. 18, 2012, the entire contents of which are incorporated herein by reference.

BACKGROUND OF THE INVENTION

1. Field of the Invention

The present invention relates to systems and methods for determining amino acid sequence of proteins or polypeptides.

2. Description of Related Art

Proteins are large organic molecules consisting of one or more polypeptide chains of amino acids. The backbone of polypeptide is linked by many peptide bonds which are formed between two adjacent amino acids by the dehydration of a carboxyl group of one amino acid and an amine group of the other amino acid. Polypeptides differ from one another primarily in their amino acid sequence. The peptide formed by two amino acids is called a "dipeptide," the peptide formed by three amino acids is called a "tripeptide," and so on.

Because the amino acid sequence determines the properties and biological functions of the proteins, it is important to find out the correct amino acid sequence of the protein [1]. In 1955, England biochemist Sanger had successfully determined the amino acid sequence of insulin and proved that the sequence is correct [2]. In addition, Perutz and Kendrew had determined the amino acid sequence of proteins by X-ray crystallography since 1958 [3-4].

Amino acids are the basic unit of proteins and are produced by fermentation, artificial synthesis, or hydrolysis of proteins. All amino acids hydrolyzed from natural proteins are α-amino acids, and typically the term "amino acids" used in biochemistry refers to α-amino acids while β-amino acids and γ-amino acids are used in the field of organic synthesis, petroleum chemical industry, and medical science. Table 1 lists 20 common amino acids found in natural proteins.

Except glycine, all α-amino acids have asymmetric carbon, and thus each of them has two enantiomers with opposite optical rotations, i.e., dextrorotatory (D) and levorotatory (L). Typically the proteins or polypeptides of organisms are constructed by levorotatory amino acids. However, exceptions may be found, for instance, tyrocidine and gramicidine also include dextrorotatory amino acids.

The hydrolysis of polypeptides may generate individual constituent amino acid residues and their enantiomers and various peptides of different lengths. Conventional high-performance liquid chromatography (HPLC) can be used for partial separation of a few hydrolytes [5-7], but fails to separate them all.

To determine the amino acid sequence, in 1984 Biemann et al. [8-9] use data from mass spectrometry to confirm the relationship between the amino acid sequence and nucleic acid sequence. In this work, proteins are hydrolyzed into peptide fragments by the mediation of trypsin, meanwhile high-performance liquid chromatography (HPLC) is used to separate peptide fragments and a fast atom bombardment-mass spectrometry (FAB-MS) is used to analyze the mass of the peptide fragments. The analysis data of FAB-MS is compared to all of the possible nucleic acid sequences, so as to confirm the relationship between the amino acid sequence and the nucleic acid sequence. At the same time, Edman develops an Edman sequencer [10-11] to determine amino acid sequence of proteins by hydrolyzing the polypeptide chain in order from N-terminal to C-terminal. Edman's method suffers from long analyzing time, poor sensitivity, and unable to separate amino acid enantiomers.

REFERENCES

[1] Bruce Alberts, Alexander Johnson, Julian Lewis, Martin Raff, Keith Robers, Peter Walter. Molecular biology of the cell, 4$^{th}$ ed. Garland Science, New York. 2002; [2] Laylin K. James, *Nobel Laureates in Chemistry* 1901-199: American Chemical Society; Chemical Heritage Foundation. Washington, D.C., 1993; [3] H. Muirhead, M. F. Perutz. "Structure of hemoglobin, three-dimensional fourier synthesis of reduced human hemoglobin at 5.5-A. resolution," Nature, 199(4894):

TABLE 1

| Name | Abbreviation | | Side chain | Molecular weight | Isoelectric point | Dissociation constant (carboxyl group) | Dissociation constant (amino group) | -log(side chain dissociation constant) (pK$_R$) |
|---|---|---|---|---|---|---|---|---|
| Glycine | G | Gly | Hydrophilic | 75.07 | 6.06 | 2.35 | 9.78 | |
| Alanine | A | Ala | Hydrophobic | 89.09 | 6.11 | 2.35 | 9.87 | |
| Valine | V | Val | Hydrophobic | 117.15 | 6 | 2.39 | 9.74 | |
| Leucine | L | Leu | Hydrophobic | 131.17 | 6.01 | 2.33 | 9.74 | |
| Isoleucine | I | Ile | Hydrophobic | 131.17 | 6.05 | 2.32 | 9.76 | |
| Phenylalanine | F | Phe | Hydrophobic | 165.19 | 5.49 | 2.2 | 9.31 | |
| Tryptophan | W | Trp | Hydrophobic | 204.23 | 5.89 | 2.46 | 9.41 | |
| Tyrosine | Y | Tyr | Hydrophilic | 181.19 | 5.64 | 2.2 | 9.21 | 10.46 |
| Aspartic acid | D | Asp | Acid | 133.1 | 2.85 | 1.99 | 9.9 | 3.9 |
| Histidine | H | His | Alkaline | 155.16 | 7.6 | 1.8 | 9.33 | 6.04 |
| Asparagine | N | Asn | Hydrophilic | 132.12 | 5.41 | 2.14 | 8.72 | |
| Glutamic acid | E | Glu | Acid | 147.13 | 3.15 | 2.1 | 9.47 | 4.07 |
| Lysine | K | Lys | Alkaline | 146.19 | 9.6 | 2.16 | 9.06 | 10.54 |
| Glutamine | Q | Gln | Hydrophilic | 146.15 | 5.65 | 2.17 | 9.13 | |
| Methionine | M | Met | Hydrophobic | 149.21 | 5.74 | 2.13 | 9.28 | |
| Arginine | R | Arg | Alkaline | 174.2 | 10.76 | 1.82 | 8.99 | 12.48 |
| Serine | S | Ser | Hydrophilic | 105.09 | 5.68 | 2.19 | 9.21 | |
| Threonine | T | Thr | Hydrophilic | 119.12 | 5.6 | 2.09 | 9.1 | |
| Cysteine | C | Cys | Hydrophilic | 121.16 | 5.05 | 1.92 | 10.7 | 8.37 |
| Proline | P | Pro | Hydrophobic | 115.13 | 6.3 | 1.95 | 10.64 | |

633-638. 1963; [4] J. Kendrew, G. Bodo, H. Dintzis, R. Parrish, H. Wyckoff, D. Phillips. "Three-dimensional model of the myoglobin molecule obtained by x-ray analysis," Nature, 181(4610): 662-666, 1958; [5] T. Ueno, M. Tanaka, T. Mastui, K. Mtasumoto. "Determination of antihypertensive small peptides, Val-Tyr and Ile-Val-Tyr, by fluorometric high-performance liquid chromatography combined with a double heart-cut column switching technique," Analytical Science, 21, 997-1000, 2005; [6] M. Gilar, P. Olivova, A. E. Daly, J. C. Gebler. "Two-dimensional separation of peptides using RP-RP-HPLC system with different pH in first and second separation dimensions," Journal of Separation Science 28, 1694-1703, 2005; [7] H. J. Issaq, K. C. Chan, J. Blonder, X. Ye, T. D. Veenstra. "Separation, detection and quantitation of peptides by liquid chromatography and capillary electrochromatography," Journal of Chromatography A, 1216, 1858-1837, 2009; [8] Chung, Deborah D. L. *The Road to Scientific Success: Inspiring Life Stories of Prominent Researchers* (*Road to Scientific Success*). World Scientific Publishing Company. 2006; [9] Gibson B. W. and Biemann K. "Strategy for the mass spectrometric verification and correction of the primary structures of proteins deduced from their DNA sequences," Proceedings of the National Academy of Sciences. 81, 1956-1960, 1984; [10] M. Kai*, M. Morizono, M. N. Wainaina, T. Kabashima, "Chemileuminescence detection of amino acids using an Edman-type reagent, 4-(1-cyanoisoindolyl) phenylisothiocyanate." Analytica Chimica Acta 535, 153-159, 2005; [11] Niall H. D. "Automated Edman degradation: the protein sequenator." Meth. Enzymol. 1973, 27: 942-1010.

SUMMARY OF THE INVENTION

An object of the present invention is to provide methods and systems to determine the amino acid sequence of polypeptides and to distinguish the enantiomers of amino acids in a fast, effective manner.

One embodiment of this invention provides a system to determine the amino acid sequence of a protein or a polypeptide. The protein or polypeptide is firstly thermally hydrolyzed to a hydrolyte, which comprises individual constituent amino acids (including enantiomers), a variety of short peptides constructed by the amino acids, and un-hydrolyzed protein or polypeptide. The system comprises a first column, a second column, and a third column. The first column connects to an ultraviolet detector, so as to separate the amino acids and short peptides. The second column connects to a fluorescence detector, so as to identify the amino acid enantiomers. The third column connects to a mass spectrometer, so as to identify the short peptides and the amino acid cysteine through the molecular weight signal (m/z) of mass spectrometry. The identified amino acid enantiomers are used to construct any possible short peptides in an order from the smallest molecular weight dipeptide to higher molecular weight short peptides, and the correct short peptides is confirmed by matching the molecular weight signal (m/z) obtained from the mass spectra. Then, the confirmed short peptides are combined to give a large peptide. The process is continued until the whole amino acid sequence of the polypeptide or protein can be determined.

Another embodiment of this invention provides a method to determine the amino acid sequence of a protein or a polypeptide, the method comprising: (1) thermally hydrolyzing the protein or the polypeptide to a hydrolyte comprising constituent amino acids (including enantiomers), a variety of short peptides constructed by the amino acid enantiomers, and un-hydrolyzed protein or polypeptide; (2) separating the amino acid enantiomers and the short peptides; (3) identifying the amino acid enantiomers; (4) identifying the short peptides using a mass spectrometer through the molecular weight signal (m/z) of mass spectra; (5) constructing any possible dipeptides by the identified amino acid enantiomers, and confirming the possible dipeptides by matching the molecular weight obtained from the mass spectra; (6) constructing any possible tripeptides by the confirmed dipeptides, and confirming the possible tripeptides by matching the molecular weight obtained from the mass spectra; (7) constructing any possible larger peptides with at least one more amino acid enantiomer residue by the confirmed short peptides (i.e., confirmed dipeptides and tripeptides), and confirming the possible larger peptides by matching the molecular weight obtained from the mass spectra; wherein step (7) is continually performed until none of the possible larger peptides can be confirmed by the molecular weight signal (m/z) of mass spectra, and whereby the amino acid sequence of the protein or the polypeptide is determined.

DETAILED DESCRIPTION OF THE PREFERRED EMBODIMENT

Figure 1A:
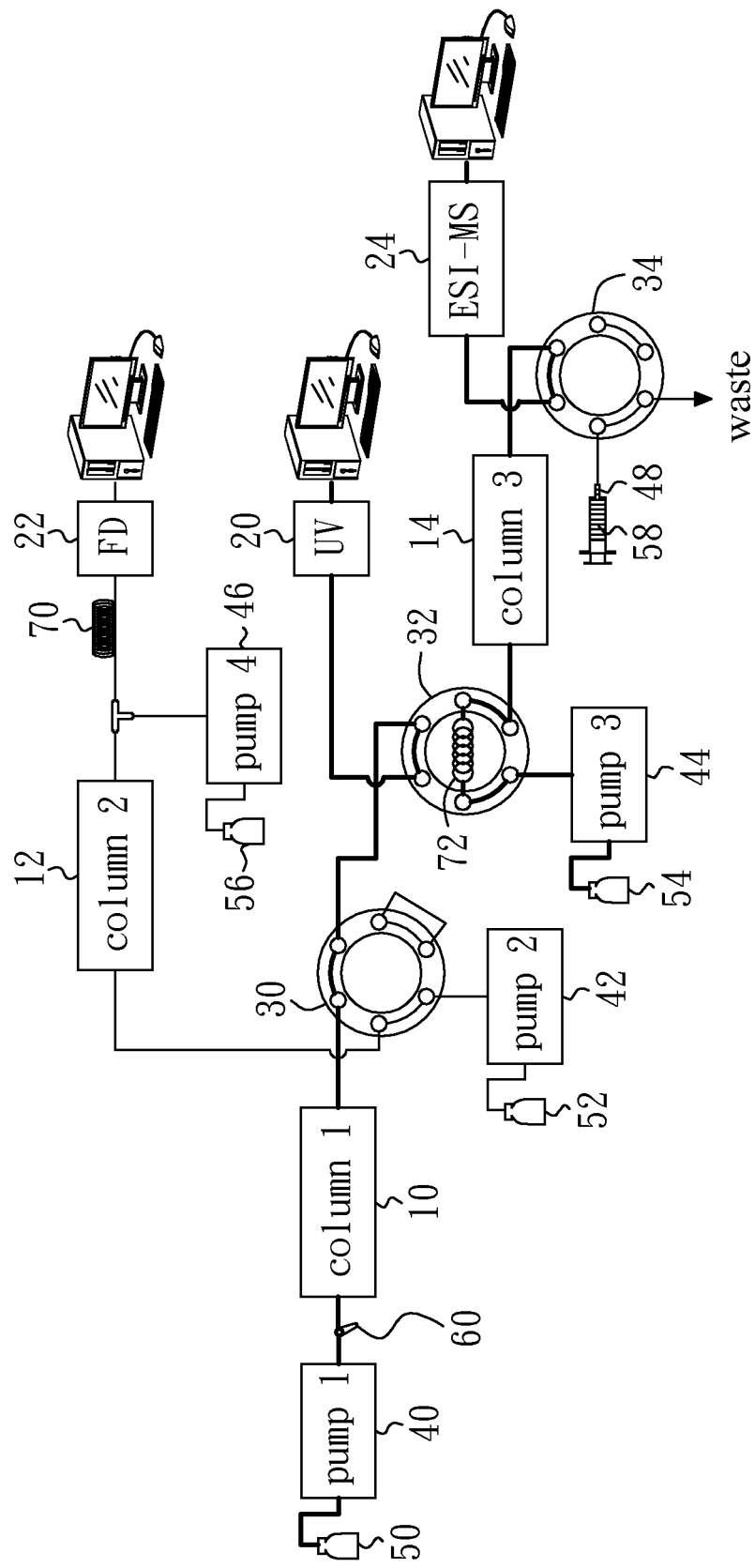
FIGS. 1A-1F show a method and system for determining the amino acid sequence of a polypeptide according to a preferred embodiment of the present invention.

Reference will now be made in detail to those specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations and components are not described in detail in order not to unnecessarily obscure the present invention. While drawings are illustrated in detail, it is appreciated that the quantity of the disclosed components may be greater or less than that disclosed, except where expressly restricting the amount of the components. Wherever possible, the same or similar reference numbers are used in drawings and the description to refer to the same or like parts.

FIGS. 1A-1F show a system and method for determining the amino acid sequence of a polypeptide or a protein. The system comprises a first column 10, a second column 12, a third column 14, a first detector 20 (ultraviolet detector 20), a second detector 22 (fluorescence detector 22), and a third detector 24 (mass spectrometer 24). In addition, the system further comprises a first pump 40, a second pump 42, a third pump 44, a fourth pump 46, and an injection syringe 48 for conveying or injecting a first mobile phase 50, a second mobile phase 52, a third mobile phase 54, a fluorescence derivatization agent 56, and a solvent 58 to the corresponding columns, fluorescence derivatization coil 70, sample loop 72, and the corresponding detectors. Further, the detectors 20/22/24 are connected to computer for the analysis work.

In this preferred embodiment, the first column 10 is an affinity chiral column (Astec ChiroBiotic™ T, 250 mm×4.6 mm I.D., particle diameter 5 μm) with a guard column ChiroBiotic™ T (30 mm×4.6 mm I.D., particle diameter 5 μm), purchased from Supelco (Bellefonte, U.S.A.). The second column 12 is a ligand-exchange column (Phenomenex Chirex 3126(D)-penicillamine, 250 mm×4.6 mm I.D., particle diameter 5 μm), with a guard column Chirex 3126(D)-penicillamine (30 mm×4.6 mm I.D., particle diameter 5 μm), purchased from Phenomenex (Torrance, U.S.A.). The third column 14 is a reversed phase column (Zorbax Eclipse XDB-C8, 150 mm×4.6 mm I.D., particle diameter 5 μm), with a guard column Zorbax Eclipse XDB-C8 (12.5 mm×4.6 mm I.D., particle diameter 5 μm), purchased from Agilent (Waldbronn, Germany).

In this preferred embodiment, the mass spectrometer 24 is an ion trap mass spectrometer (Brucker Daltonics, Esquire 2000, Billerica, U.S.A.) coupled with an Electrospray Ionization Interface (ESI).

In this preferred embodiment, both the first mobile phase 50 and the second mobile phase 52 are 2 mM $CuSO_4$/MeOH solution with a volume ratio (v/v) 90/10, and the third mobile phase 54 and the solvent 58 are 100% methanol. The fluorescence derivatization agent 56 is prepared as follows. Firstly, 900 mL of deionized distilled water and 3.8138 g of $Na_2B_4O_7 \cdot 10H_2O$ are added in a container to form a solution. Then 5 mM NaOH aqueous solution is used to adjust the pH of the solution to 9.5. Then deionized distilled water is added to the solution till the total volume of the solution is 1000 mL, and hence a 0.01 M borate buffer solution is prepared. After that, 2.146 g of o-phthaldialdehyde (OPA) and 1 mL of mercaptoethanol ($C_2H_6OS$) are added to the buffer solution, and the solution is shaken in an orbital-shaking incubator at 30° C., 150 rpm for one day, such that the fluorescence derivatization agent 56 is prepared. The fluorescence derivatization agent 56 is used to derivatize the amino acids so that they can be analyzed by the fluorescence detector 22.

According to the embodiment, a protein or a polypeptide under test is needed to be thermally hydrolyzed by the following procedure. 1 mL of the 1000 ppm standard protein or polypeptide solution is taken and placed into one well of a 20-well array platform reactor which is controlled at a predetermined temperature. The reaction time is about 1 day to 4 days. After the hydrolysis, the hydrolyte is taken out and deionized distilled water is added to the hydrolyte so as to dilute the concentration by 10-fold. A syringe filter is used to filter the hydrolyte. The filtrate will be used later.

It should be noted that the temperature for the hydrolysis can be controlled so that the protein or polypeptide is partially hydrolyzed rather than completely hydrolyzed. For example, if the protein or the polypeptide is a tripeptide, the hydrolysis temperature is controlled so that it is hydrolyzed to an unhydrolyzed tripeptide, two kinds of dipeptide, and three kinds of amino acid enantiomers.

Figure 1B:
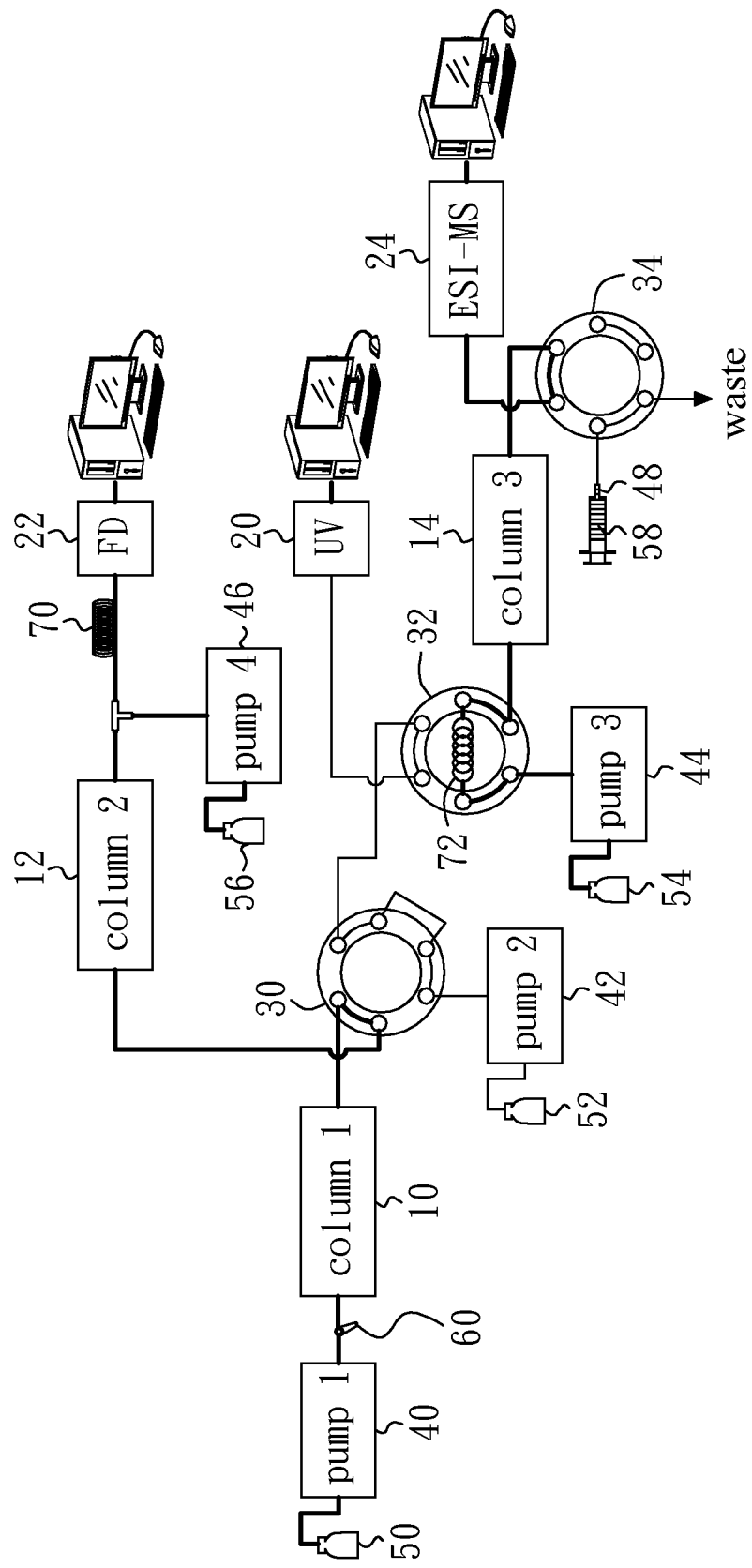
Figure 1C:
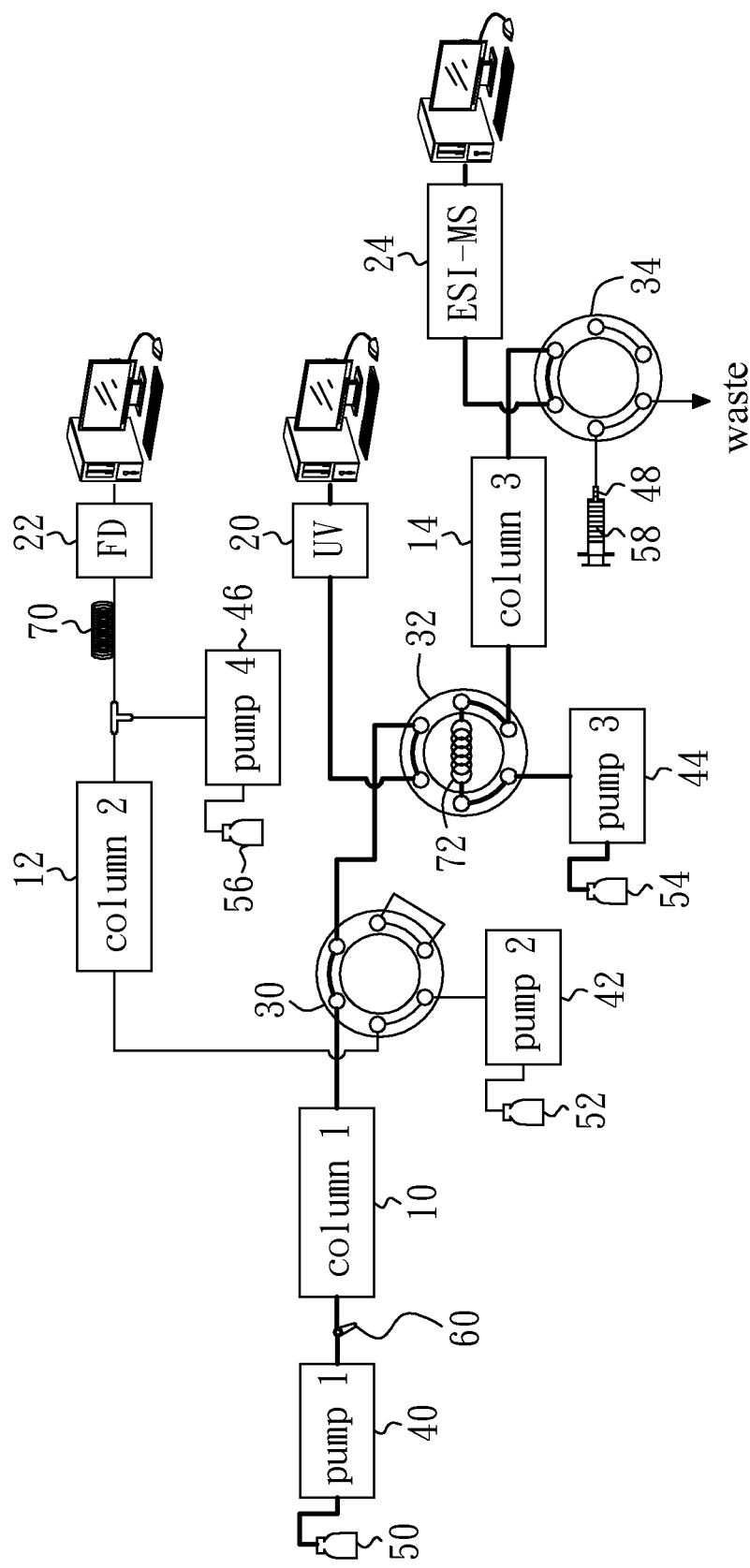
Figure 1D:
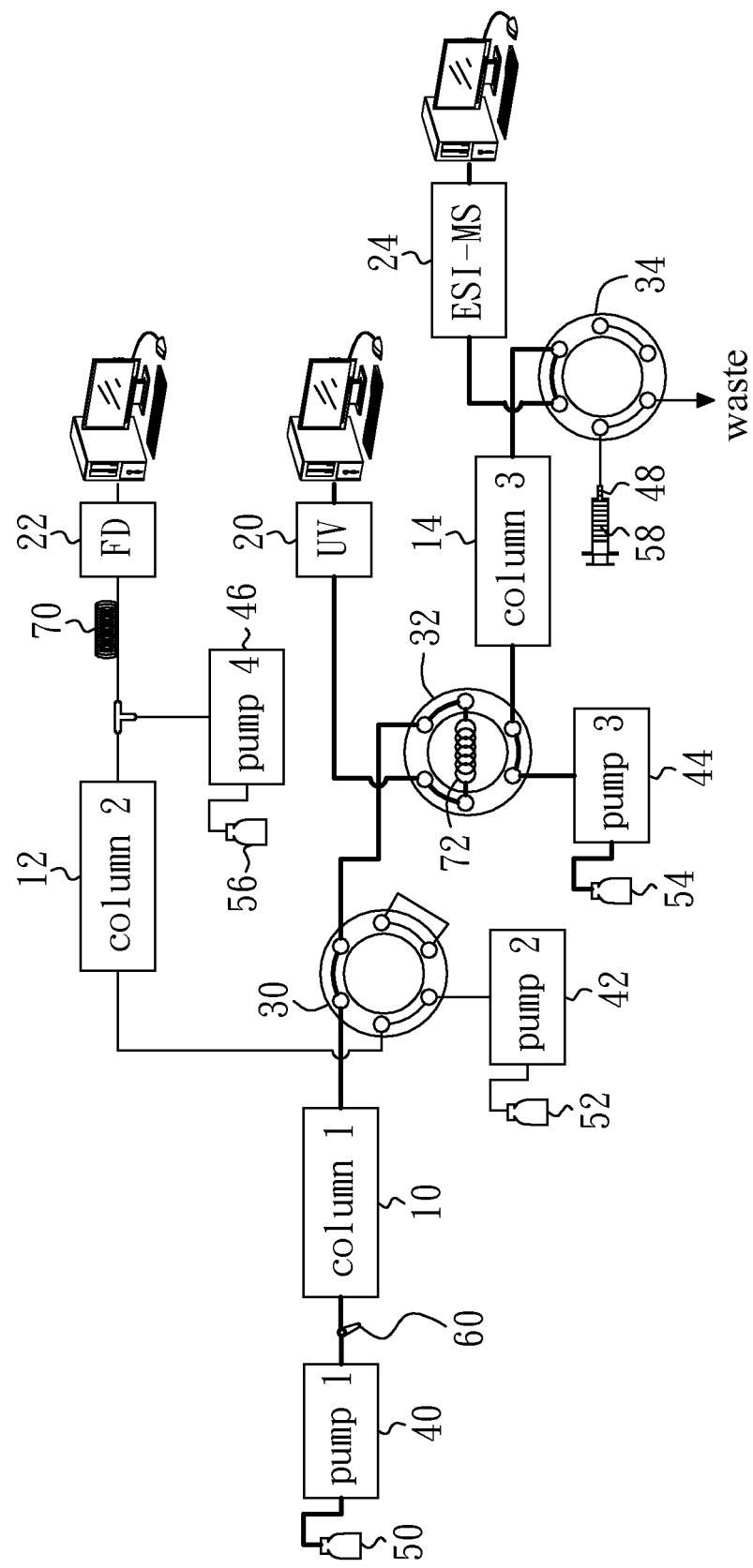
Figure 1E:
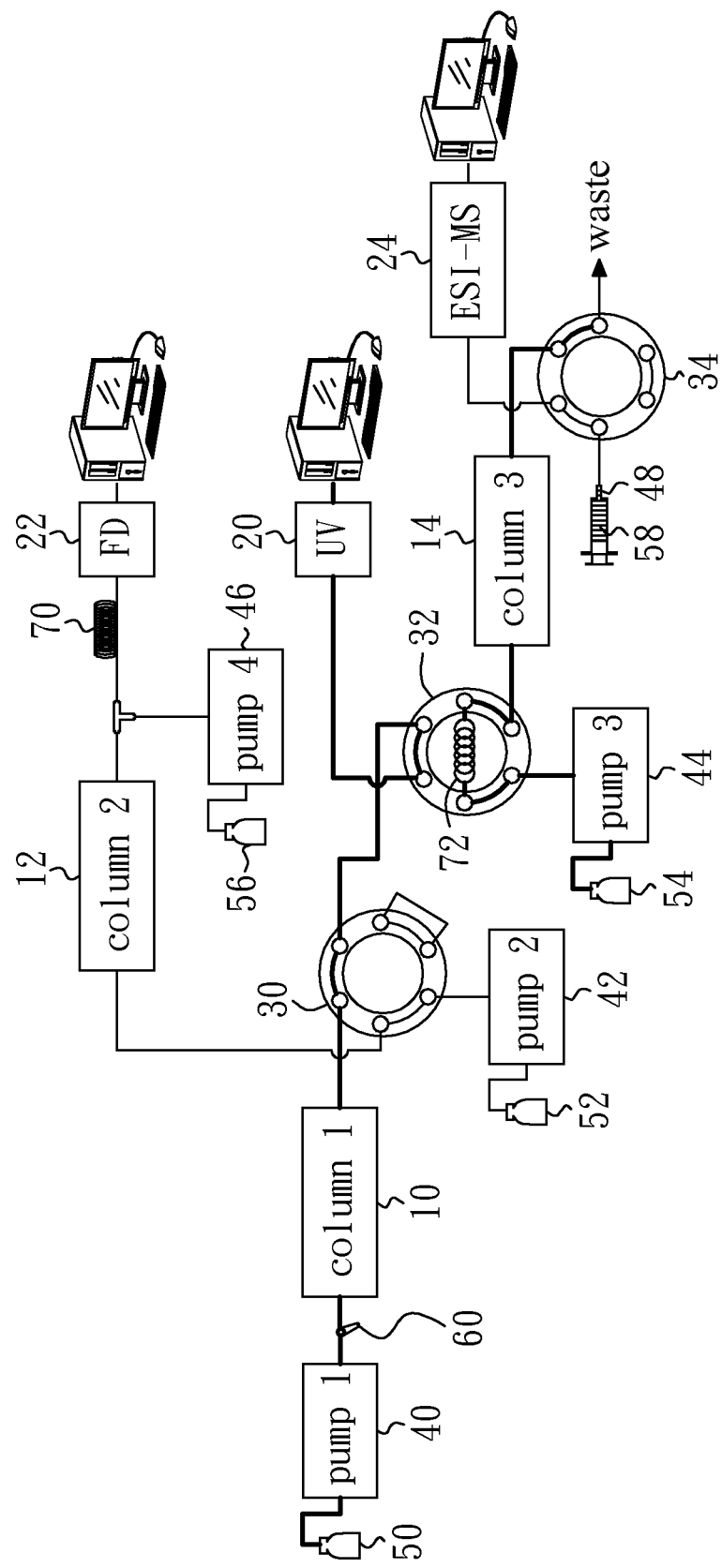
Figure 1F:
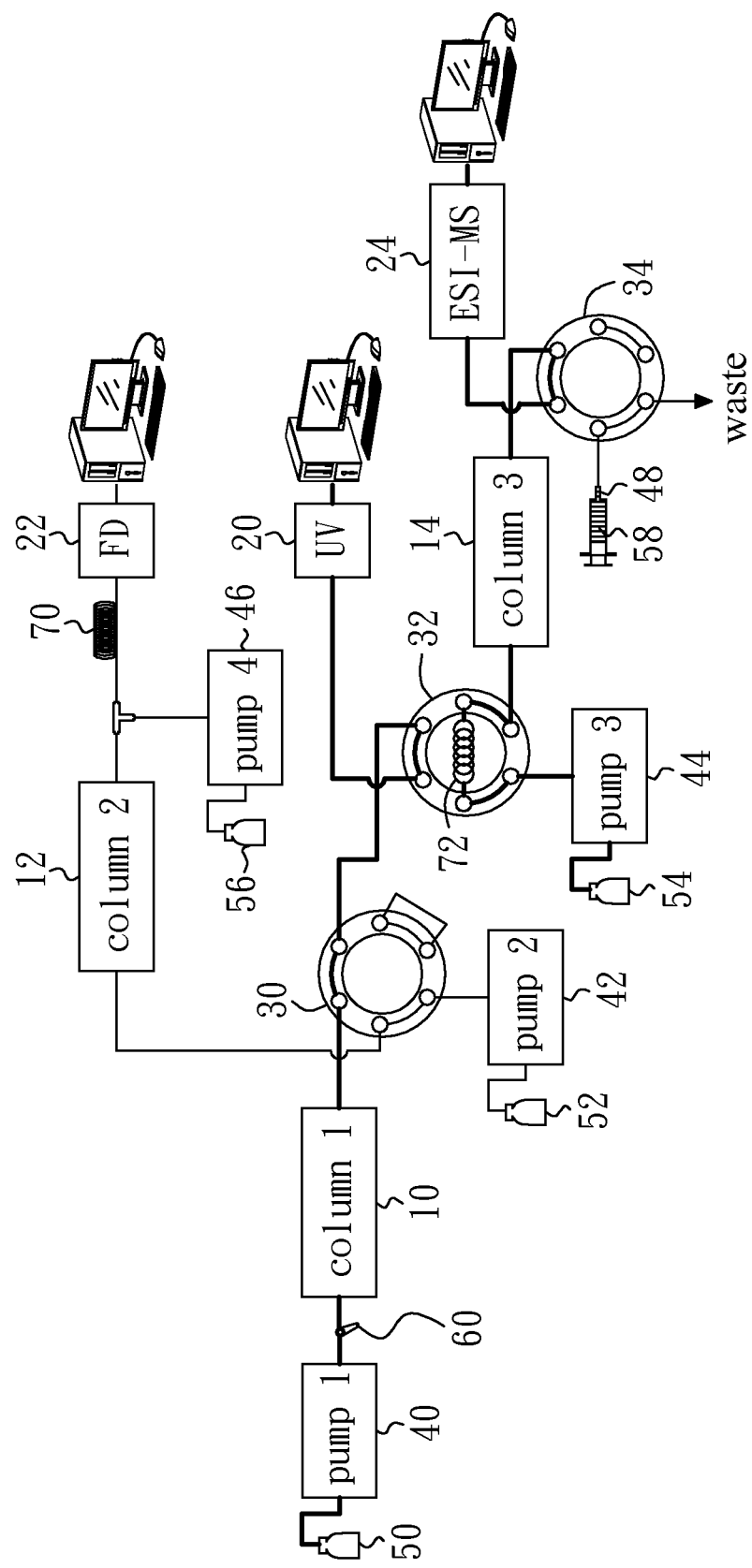

The procedure for determining the amino acid sequence of the protein or polypeptide is described as follows. As shown in FIG. 1A, the above-mentioned filtered hydrolyte is injected into the first column 10 via a syringe injection valve 60 to separate amino acids and short peptides of the hydrolyte. Then, as shown in FIG. 1B, when the amino acids will be eluted out of the first column 10, the valve 30 is switched to connect the first column 10 and the second column 12 in series, and the amino acids in the hydrolyte flow into the second column 12. The second column 12 separates the amino acid enantiomers, and the fluorescence derivatization agent (OPA) 56 reacts with the amino acid enantiomers to transfer them in a form for being analyzed by the fluorescence detector 22. As shown in FIG. 1C, when the amino acid enantiomers completely flow into the second column 12, the valve 30 is switched back to its original position. As shown in FIG. 1D, when the short peptides will be eluted out from the first column 10, the valve 32 is switched, such that the short peptides can flow into the sampling loop 72. Then, as shown in FIG. 1E, when the short peptides completely flow into the sampling loop 72, the valve 32 and valve 34 are simultaneously switched, such that the third mobile phase 54 (100% methanol) can carry the short peptides in the sampling loop 72 into the third column 14 to separate the short peptides and the copper ions. At this time, the third mobile phase elutes the sulphate ions and copper ions first out of the third column 14 to flow into the waste collection bottle, and the injection syringe 48 continually injects methanol 58 into the mass spectrometer 24 because the third column 14 is not yet connected to the mass spectrometer 24. As shown in FIG. 1F, after wait about 30 seconds, the valve 34 is switched, so that the third column 14 and the mass spectrometer 24 are connected in series and the short peptides out from the third column 14 can be analyzed by mass spectrometer 24.

The enantiomers of amino acids are detected by the fluorescence detector 22 whose excitation wavelength is 340 nm and emission wavelength is 450 nm; the amino acids and the short peptides are detected by the ultraviolet detector at wavelength 254 nm. The mass spectrometer 24 is an ion trap mass spectrometer with Electrospray Ionization Interface (ESI) in which both the nebulizing gas and the drying gas are nitrogen, the pressure and flow rate for the nebulizing gas are 20.0 psi and 5 L min$^{-1}$, respectively, and the temperature of the drying gas is 300° C.

The mass spectrum signal (m/z) was detected in a positive ion mode. The capillary inlet voltage and outlet voltage, the skimmer 1 voltage, and the ion trap driving voltage are set as 4500, 38.2, 31.5, and 36.3 V, respectively. The mass-to-charge ratio (m/z) is set at a range between 50 and 1000. Because the flow rate (1 mL min$^{-1}$) of the mobile phase 54 out from the third column 14 is too large for the ESI, a flow rate splitter is used to lower the flow rate of the eluent into the ESI.

In this embodiment, the protein or polypeptide is thermally hydrolyzed to short peptides and amino acids, and a three-dimensional HPLC is used to separate them step by step. In addition, the enantiomers of the amino acids can be separated and used for the determination of amino acid sequence as well. In particular, the first column 10 is used to separate the short peptides and the amino acids, the second column 12 is used to separate the enantiomers of amino acids, and the third column is used to separate the short peptides, copper ions, and sulfate ions, and when the mobile phase is changed to methanol, the mass spectrometer 24 is used to analyze short peptides and cysteine.

Because the short peptides and the amino acids have similar structure, polarity, size, and physical properties, the selection of suitable first column 10 is difficult. In this embodiment, four different columns have been tested to separate standard short peptides. They are Eclipse XDB-C8, Juipter C4, Chromolith® RP-18e, and Astec ChiroBiotic™ T. In this embodiment, the polypeptide to be determined is glutathione. After the experiments, only Astec ChiroBiotic™ T can separate the amino acids and short peptides produced from glutathione hydrolsis. In addition, it is found that a low concentration of copper ions should be added in the mobile phase to increase the selectivity of the column.

Figure 2:
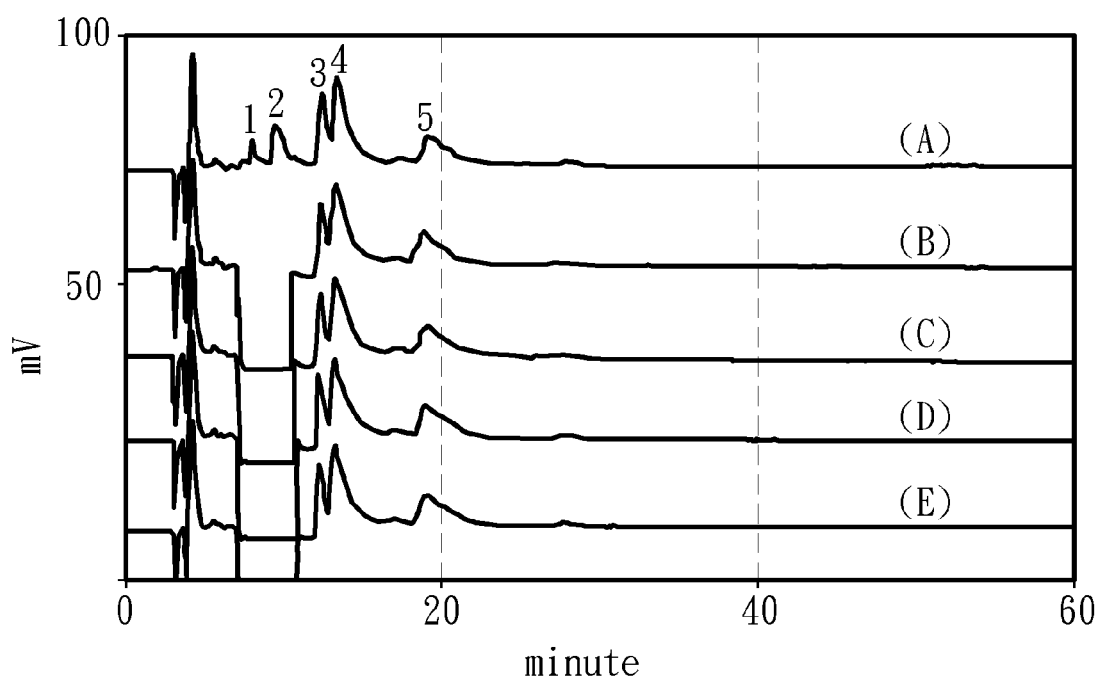
FIG. 2 shows the chromatogram of the first column according to the preferred embodiment of the present invention.

FIG. 2 shows the chromatogram of the first column 10 with different switching time, in which the five peaks respectively represent: peak 1, L-glutamic acid (Glu); peak 2, glycine (Gly); peak 3, dipeptide Glu-Gly; peak 4, dipeptide Cys-Gly; peak 5, glutathione. In addition, the second switching time of valve 30 is at: A, 0.0 min; B, 10.5 min; C, 10.6 min; D, 10.7 min; and E, 10.8 min.

Figure 3:
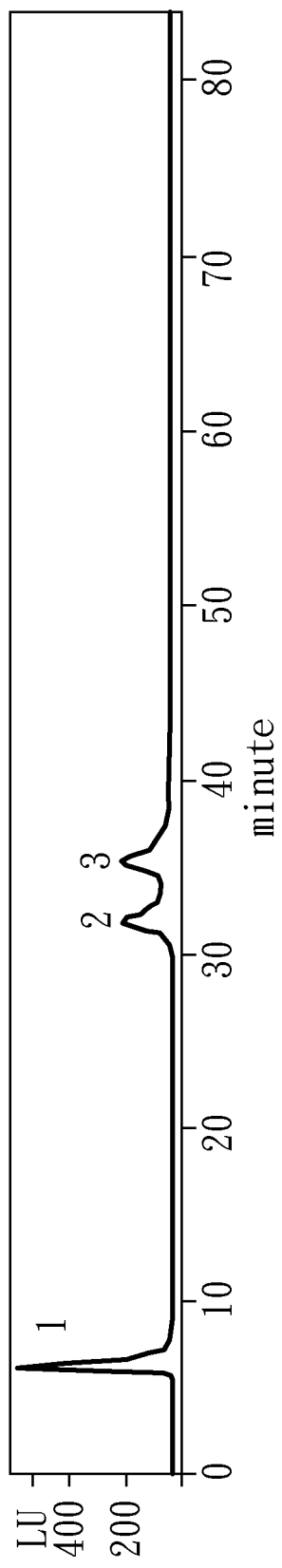
FIG. 3 shows the chromatogram of the second column according to the preferred embodiment of the present invention.

FIG. 3 shows the chromatogram of the second column 12, in which the three peaks respectively represent: peak 1, glycine (Gly); peak 2, L-glutamic acid (L-Glu); peak 3, D-glutamic acid (D-Glu). The second column 12 is Chirex 3126(D)-penicillamine. The copper ions of the mobile phase and the enantiomers of the amino acids respectively form complex compounds with different stability, which can proceed the exchange of ligand with the packed single chiral enantiomer within the second column 12, so as to separate the enantiomers of amino acids. The experimental results show that if the concentration of methanol in the mobile phase is gradually increased, the analysis time is gradually decreased, but the separation efficiency is gradually decreased as well. After some experiments, the concentration of methanol is determined to be 10% (v/v) in the mobile phase.

In this embodiment, the switching times of the valves are important. If the switching times are improper, a part of the sample may be lost, resulting in lower sensitivity and causing analysis error. Therefore the columns should be switched at proper time. In this embodiment, after the hydrolyte is separated by the first column 10, several switching times are tested according to the peak positions and their retention times. Then the short peptides and the enantiomers are detected individually by the fluorescence detector 22 and the peak area of them is calculated. The statistical method One-way Analysis of Variance (ANOVA) is used to compare the peak areas obtained from the different switching time and followed by the least significant test to determine the optimum switching time. In this embodiment, the protein or polypeptide to be test is glutathione, and after a series of experiments, it is determined that the valve 30 is firstly switched at 7.0 min and secondly switched at 10.7 min.

Figure 4:
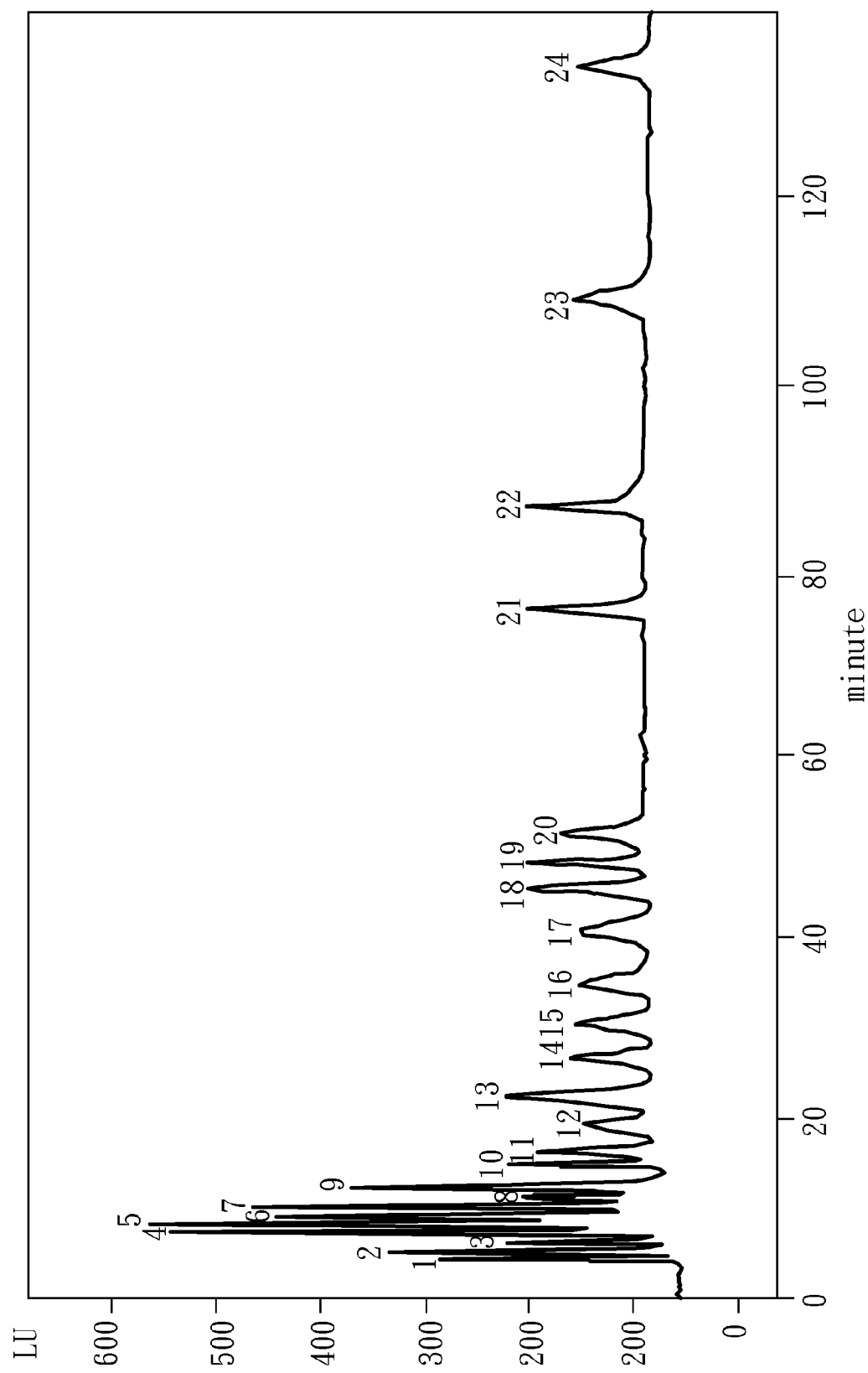
FIG. 4 shows the chromatogram of the second column according to the preferred embodiment, in which 24 standard amino acid enantiomers are separated by the second column.

To investigate the capability of separating enantiomers by the second column 12, the second column 12 is used to isocratically separate 20 common amino acids and their dextrorotatory (D) and levorotatory (L) enantiomers by grouping them into three groups so that they can be resolved within each group. Table 2 lists the result. Most enantiomers have a resolution greater than or approaching to 1.0; therefore the second column 12 has an excellent capability to separate the enantiomers of the amino acids. However, because cysteine has a thiol group (—SH) which may form precipitate with copper ions, the second column 12 cannot identify cysteine. After that, according to the retention times, the 20 common dextrorotatory (D) and levorotatory (L) enantiomers are divided into three groups. One or more enantiomers of each group, whose peaks are completely resolved by isocratic elution, are selected, mixed, and eluted by gradient elution, so as to reduce the analysis time. According to the chromatogram of the gradient elution, other enantiomers are added and separated by the gradient elution with same conditions. FIG. 4 shows the final chromatogram in which 24 enantiomers of amino acids can be simultaneously separated by the second column. The 24 enantiomers of amino acids are: (1) L-Lys, (2) D-Lys, (3) D-Arg, (4) Gly, (5) L-Ala, (6) D-Ser, (7) D-Thr, (8) D-Gln, (9) L-Pro, (10) L-Val, (11) L-His, (12) D-Pro, (13) D-Val, (14) L-Met, (15) L-Asp, (16) L-Ile, (17) D-Asp, (18) L-Glu, (19) D-Glu, (20) D-Leu, (21) L-Phe, (22) D-Phe, (23) L-Trp, (24) D-Trp.

TABLE 2

| Name | abbreviation | Side chain | L-(retention time)[a] | D-(retention time) | resolution |
|---|---|---|---|---|---|
| Glycine | G | Gly | Hydrophilic | 5.50 | — |
| Alanine | A | Ala | Hydrophobic | 5.77 | 7.14 | 3.04 |
| Valine | V | Val | Hydrophobic | 12.37 | 19.16 | 4.68 |
| Leucine | L | Leu | Hydrophobic | 44.08 | 46.94 | 1.10 |
| Isoleucine | I | Ile | Hydrophobic | 26.86 | 30.53 | 1.33 |
| Phenylalanine | F | Phe | Hydrophobic | 78.31 | 109.43 | 4.45 |
| Tryptophan | W | Trp | Hydrophobic | 151.53 | 226.34 | 9.45 |
| Tyrosine | Y | Tyr | Hydrophilic | 25.38 | 31.22 | 1.98 |
| Aspartic acid | D | Asp | Acid | 24.52 | 30.99 | 3.5 |
| Histidine | H | His | Alkaline | 15.73 | 19.33 | 2.58 |
| Asparagine | N | Asn | Hydrophilic | 6.011 | 6.003 | — |
| Glutamic acid | E | Glu | Acid | 41.46 | 45.58 | 1.29 |
| Lysine | K | Lys | Alkaline | 3.73 | 4.14 | 1.00 |
| Glutamine | Q | Gln | Hydrophilic | 6.05 | 7.03 | 1.85 |
| Methionine | M | Met | Hydrophobic | 21.70 | 27.49 | 2.14 |
| Arginine | R | Arg | Alkaline | 4.19 | 4.94 | 1.39 |
| Serine | S | Ser | Hydrophilic | 5.84 | 6.21 | 0.74 |
| Threonine | T | Thr | Hydrophilic | 6.31 | 6.94 | 0.90 |
| Cysteine | C | Cys | Hydrophilic | — | — | — |
| Proline | P | Pro | Hydrophobic | 7.63 | 16.69 | 8.05 |

[a]Retention time is an average after four measurements.
[b]Separation conditions: Column temperature 40° C., sample injection volume 20 μL, ultraviolet detector wavelength 254 nm, mobile phase flow rate 1 mL min$^{-1}$, and mobile phase MeOH/2 mM CuSO$_4$ = 10/90 (v/v).

Then, the detection limit of the fluorescence detector 22 is investigated. Firstly high concentration amino acid enantiomers standard solutions are prepared then diluted to 0 μg mL$^{-1}$, 0.25 μg mL$^{-1}$, 0.5 μg mL$^{-1}$, 1.0 μg mL$^{-1}$, 2.5 μg mL$^{-1}$, and 5.0 μg mL$^{-1}$ and each concentration of standard solution is measured for 5 times in which the lowest 4 concentrations of standard solution are selected to prepare the calibration curve. The detection limit is determined from the calibration curve. Each of the 20 common dextrorotatory (D) and levorotatory (L) enantiomers of amino acids is used to make the calibration curves, respectively. The results show that the detection limit of the fluorescence detector 22 is between 0.1-0.2 µg mL$^{-1}$, which is superior to the ultraviolet detectors used in the literatures.

To investigate the sensitivity of the mass spectrometer 24, the present invention uses reduced form glutathione (formed by glutamic acid, cysteine, and glycine) and two kinds of hydrolyzed dipeptide (Cys-Gly and γ-Glu-Cys) to prepare the external standard calibration curve, and the lowest 5 concentrations (0, 1.0, 2.5, 5.0, 7.5 µg mL$^{-1}$) are used to make the calibration curves and each standard solution is measure 3 times. The detection limit and the quantitative limit are determined from the calibration curves. The results show that the detection limit and the quantitative limit of glutathione are 0.9 and 3.1 µg mL$^{-1}$, respectively, and 1.1 and 3.6 µg mL$^{-1}$ for Cys-Gly, and 0.9 and 3.1 µg mL$^{-1}$ for γ-Glu-Cys.

This invention uses a self-designed 20-well array reactor for the hydrolysis reaction. The hydrolysis reaction may take 1-4 days at a predetermined temperature. Table 3 lists the analysis result of the hydrolyte of glutathione from 1 day to 4 days hydrolysis at 90° C. In the preferred embodiment, glutathione is hydrolyzed for 1 day and the hydrolyte is used to determine the amino acid sequence.

gram. The following two examples respectively illustrate the procedure used to determine the amino acid sequence of glutathione and aspartame.

The reduced form glutathione is a tripeptide constituted by L-glutamic acid, L-cysteine, and glycine. Firstly, the qualitative analysis of the hydrolyte using the second column 12 identifies glycine and L-glutamic acid. Because the second column cannot identify L-cysteine, the molecular weight signal (m/z) of mass spectrometry is used to investigate if L-cysteine is present. Since the molecular weight signal (m/z) of mass spectrometry shows a signal with mass-to-charge ratio (m/z) 122.1 corresponding to cysteine, it is confirmed that glutathione has three amino acid, i.e., glycine, L-glutamic acid, and L-cysteine.

After that, the identified amino acids are combined to construct any possible dipeptides. If X, Y, and Z denote L-glutamic acid (Glu), L-cysteine (Cys), glycine (Gly), respectively, then the possible dipeptides include XX, YY, ZZ, XY, YX, YZ, ZY, XZ, and ZX. Since the molecular

TABLE 3

| | 3D-HPLC-FD system | | | | | | 3D-HPLC-ESI-MS system | | | | | |
|---|---|---|---|---|---|---|---|---|---|---|---|---|
| Temp °C. | Time (day) | Gly (ppm) | RSD (%) | L-Glu (ppm) | RSD (%) | D-Glu (ppm) | RSD (%) | Cys-Gly (ppm) | RSD (%) | Glu-Cys (ppm) | RSD (%) | Glutathione (ppm) | RSD (%) |
| 90 | 1 | 2.2 ± 0.1 | 4.7 | 3.5 ± 0.1 | 2.8 | — | — | 3.1 ± 0.6 | 19.1 | 1.2 ± 0.2 | 21.8 | 11.5 ± 2.1 | 17.9 |
| 90 | 2 | 6.2 ± 0.4 | 6.3 | 6.8 ± 0.4 | 6.4 | — | — | 4.1 ± 0.7 | 16.8 | 1.4 ± 0.2 | 18.7 | 5.4 ± 1.2 | 22.2 |
| 90 | 3 | 8.2 ± 0.1 | 1.6 | 11.3 ± 0.4 | 3.7 | — | — | 6.5 ± 0.8 | 12.3 | 1.4 ± 0.4 | 32.1 | 4.1 ± 0.7 | 17.3 |
| 90 | 4 | 13.3 ± 0.2 | 1.6 | 10.6 ± 0.3 | 2.8 | 0.6 ± 0.1 | 14.2 | 6.4 ± 0.7 | 11.1 | 1.8 ± 0.3 | 12.4 | 1.7 ± 0.4 | 23.7 |

In another embodiment of this invention, aspartame is used as the polypeptide to determine its amino acid sequence. Aspartame is a dipeptide constituted by aspartic acid (Asp) and phenylalanine (Phe). Table 4 lists the quantitative analysis of its hydrolyte at 90° C. and 1-4 days reaction period. In the preferred embodiment, Aspartame is hydrolyzed for 1 day and the hydrolyte is used to determine the amino acid sequence.

weight signal (m/z) of mass spectrometry did not show dipeptides constituted with same amino acids, Table 5 lists only the 6 molecular weight signal (m/z) of mass spectrometry of dipeptide fragments in the hydrolyte constituted by different amino acids. By comparing the molecular weight signal (m/z) of mass spectrometry, the dipeptides XY (Glu-Cys, m/z=251.3) and YZ (Cys-Gly, m/z=179.32) are confirmed.

TABLE 4

| | 3D-HPLC-FD system | | | | | | | | 3D-HPLC-ESI-MS system | |
|---|---|---|---|---|---|---|---|---|---|---|
| Temp °C. | Time (day) | L-Asp (ppm) | RSD (%) | D-Asp (ppm) | RSD (%) | L-Phe (ppm) | RSD (%) | D-Phe (ppm) | RSD (%) | Aspartame (ppm) | RSD (%) |
| 90 | 1 | 3.7 ± 0.1 | 2.6 | — | — | 3.1 ± 0.2 | 6.5 | — | — | 11.4 ± 1.4 | 21.8 |
| 90 | 2 | 10.8 ± 0.3 | 2.4 | 2.9 ± 0.1 | 3.5 | 5.7 ± 0.2 | 3.5 | — | — | 5.2 ± 0.8 | 18.7 |
| 90 | 3 | 10.6 ± 0.3 | 2.7 | 3.1 ± 0.1 | 3.4 | 6.8 ± 0.3 | 4.2 | — | — | 2.1 ± 0.4 | 32.1 |
| 90 | 4 | 8.7 ± 0.2 | 2.2 | 2.8 ± 0.1 | 3.5 | 6.4 ± 0.3 | 4.8 | — | — | — | — |

After the amino acid enantiomers of the hydrolyte are identified by the second column 12, the ESI-mass spectrometer 20 is used to measure the molecular weight of the short peptides of the hydrolyte from the obtained mass spectra signal (m/z). The amino acid enantiomers identified by the second column 12 are combined to construct any possible short peptides in an order from the smallest molecular weight dipeptide to higher molecular weight short peptides, and the correct short peptides is confirmed by matching the molecular weight signal (m/z) obtained from the mass spectrometry. The confirmed possible short peptides are combined to construct any possible longer peptides and confirmed by the molecular weight signal (m/z) of mass spectrometry. The procedure is repeated until the correct amino acid sequence is found. The procedure can also be assisted by computer pro-

TABLE 5

| Dipeptide | MS(+) fragment (cnts) | | |
|---|---|---|---|
| [Glu-Cys] (250.3 Da) | [GluCys + H]$^+$ (m/z 251.3) 904 | [GluCys + Na]$^+$ (m/z 273.3) 467 | [GluCys − Cys]$^+$ (m/z 130.1) 584 |
| [Cys-Glu] (250.3 Da) | [CysGlu + H]$^+$ (m/z 251.3) 904 | [CysGlu + Na]$^+$ (m/z 273.3) 467 | [CysGlu − Glu]$^+$ (m/z 104.1) 455 |
| [Glu-Gly] (204.2 Da) | [Glu-Gly + H]$^+$ (m/z 205.2) — | [GluGly + Na]$^+$ (m/z 227.2) 586 | [GluGly − Gly]$^+$ (m/z 130.1) 584 |
| [Gly-Glu] (204.2 Da) | [GlyGlu + H]$^+$ (m/z 205.2) — | [GlyGlu + Na]$^+$ (m/z 227.2) 586 | [GlyGlu − Glu]$^+$ (m/z 58.1) — |

TABLE 5-continued

| Dipeptide | MS(+) fragment (cnts) | | |
|---|---|---|---|
| [Gly-Cys] (178.2 Da) | [GlyCys + H]$^+$ (m/z 179.2) 1669 | [GlyCys + Na]$^+$ (m/z 201.2) 1330 | [GlyCys − Cys]$^+$ (m/z 58.1) — |
| [Cys-Gly] (178.2 Da) | [CysGly + H]$^+$ (m/z 179.2) 1669 | [CysGly + Na]$^+$ (m/z 201.2) 1330 | [CysGly − Gly]$^+$ (m/z 104.1) 455 |

2. (Glu-Gly-Cys)

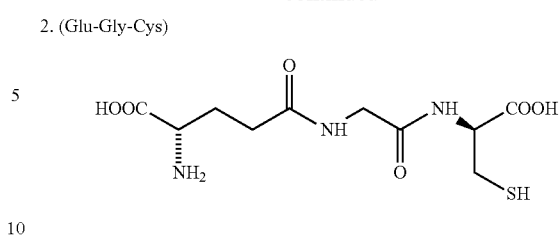

TABLE 6

| Tripeptide | MS(+) fragment (cnts) | | | |
|---|---|---|---|---|
| [Glu-Cys-Gly] (307.3 Da) | [M + H]$^+$ (m/z 308.3) 16559 | [M + Na]$^+$ (m/z 330.3) 2807 | [M − Gly]$^+$ (m/z 233.3) 9387 | [M − CysGly]$^+$ (m/z 130.1) 36411 |
| [Cys-Glu-Gly] (307.3 Da) | [M + H]$^+$ (m/z 308.3) 16559 | [M + Na]$^+$ (m/z 330.3) 2807 | [M − Gly]$^+$ (m/z 233.3) 9387 | [M − GluGly]$^+$ (m/z 104.1) — |
| [Glu-Gly-Cys] (307.3 Da) | [M + H]$^+$ (m/z 308.3) 16559 | [M + Na]$^+$ (m/z 330.3) 2807 | [M − Cys]$^+$ (m/z 187.2) 7480 | [M − GlyCys]$^+$ (m/z 130.1) 36411 |
| [Gly-Glu-Cys] (307.3 Da) | [M + H]$^+$ (m/z 308.3) 16559 | [M + Na]$^+$ (m/z 330.3) 2807 | [M − Cys]$^+$ (m/z 187.2) 7480 | [M − GluCys]$^+$ (m/z 58.1) — |
| [Gly-Cys-Glu] (307.3 Da) | [M + H]$^+$ (m/z 308.3) 16559 | [M + Na]$^+$ (m/z 330.3) 2807 | [M − Glu]$^+$ (m/z 161.2) 4871 | [M − CysGlu]$^+$ (m/z 58.1) — |
| [Cys-Gly-Glu] (307.3 Da) | [M + H]$^+$ (m/z 308.3) 16559 | [M + Na]$^+$ (m/z 330.3) 2807 | [M − Glu]$^+$ (m/z 161.2) 4971 | [M − GlyGlu]$^+$ (m/z 104.1) — |

The confirmed dipeptides XY and YZ are combined to construct any possible tripeptides. There is only one possible tripeptide, i.e., XYZ (Glu-Cys-Gly) and is confirmed by the molecular weight signal (m/z=308.3) of mass spectrometry. Then, the confirmed dipeptides XY and YZ and tripeptide XYZ are combined to construct any possible tetrapeptides; however, no molecular weight signal (in/z) of mass spectrometry to show any possible tetrapeptide. Then, the confirmed dipeptides XY and YZ and tripeptide XYZ are combined to construct any possible pentapeptides. The possible pentapeptides include XYZXY, XYXYZ, XYZYZ, and YZXYZ. However, none of the possible pentapeptides can match the molecular weight signal (m/z) of mass spectrometry. Finally, the confirmed dipeptides XY and YZ and tripeptide XYZ are combined to construct any possible hexapeptides. The only possible hexapeptide is XYZXYZ, which cannot match the molecular weight signal (m/z) of mass spectrometry. Therefore, it is confirmed that the polypeptide is a tripeptide. Table 3 lists all tripeptides formed by Glu, Cys, and Gly and their mass fragment molecular signal. By comparing the mass fragment molecular signal, it is judged that the following two tripeptides are matched:

1. (Glu-Cys-Gly)

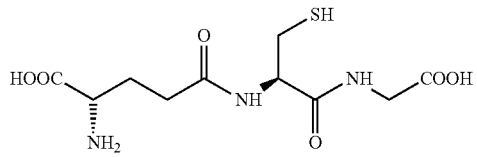

However, by checking the mass spectra fragment signal of dipeptides listed in Table 5, it can be found only number 1 tripeptide, i.e., Glu-Cys-Gly, is matched. Thus the amino acid sequence of the polypeptide is confirmed as Glu-Cys-Gly.

In another example, Aspartame is used as the polypeptide to determine its amino acid sequence. Aspartame is a methyl ester dipeptide formed by aspartic acid (Asp) and phenylalanine (Phe) methyl ester. In this example, Aspartame is hydrolyzed to un-hydrolyzed aspartame, L-aspartic acid, L-phenylalanine, and methanol.

Firstly, the polypeptide can be identified by the second column 12 to have two kinds of amino acid enantiomers, L-aspartic acid and L-phenylalanine. In addition, the molecular weight signal (m/z) of mass spectrometry of the hydrolyte obtained from the mass spectrometer 24 cannot find a mass-to-charge ratio (m/z) 122.1 corresponding to cysteine. Therefore, it confirms that aspartame has only two constituent amino acids, L-aspartic acid (Asp) and L-phenylalanine (Phe).

Then, L-aspartic acid (Asp) and L-phenylalanine (Phe) are combined to construct any possible dipeptides. If X and Y denote L-aspartic acid and L-phenylalanine, respectively, then the possible dipeptides includes XX, YY, XY, and YX. By comparing with the molecular weight signal (m/z) of mass spectrometry, the confirmed present dipeptides is XY (Asp-Phe, m/z=280.3). However, the mass fragment signal is weak and it is deduced that some other group may modify this dipeptide. By trial-and-error, some common groups are used to modify XY, and the modified dipeptide XY is checked if the molecular weight signal (m/z) of mass spectrometry can be matched. This is a troublesome work. Finally, a modified XY, Asp-Phe-OCH$_3$ is confirmed by the molecular weight signal (m/z) of mass spectrometry and it is determined the amino acid sequence of the polypeptide is Asp-Phe-OCH$_3$. Table 7 lists the mass fragment signals of dipeptides in this example.

TABLE 7

| Dipeptide | MS(+) fragment | | | | |
|---|---|---|---|---|---|
| [Asp-Phe] (280.3 Da) | [Asp-Phe + H]$^+$ (m/z 281.3) 4079 | [AspPhe + Na]$^+$ (m/z 303.3) 1693 | [AspPhe – Phe]$^+$ (m/z 116.2) 1140 | [Phe + H]$^+$ (m/z 166.1) 7593 | |
| [Phe-Asp] (280.3 Da) | [PheAsp + H]$^+$ (m/z 281.3) 4079 | [PheAsp + Na]$^+$ (m/z 303.3) 1693 | [PheAsp – Asp]$^+$ (m/z 148.1) 1370 | [Asp + H]$^+$ (m/z 134.2) 1930 | |
| [Asp-Phe]ME (294.3 Da) | [AspPhe + H]$^+$ (m/z 295.3) 10081 | [AspPhe + Na]$^+$ (m/z 317.2) 1033 | [AspPhe – Phe]$^+$ (m/z 116.2) 1140 | [Phe + H]$^+$ (m/z 180.3) 8761 | |
| [Phe-Asp]ME (294.3 Da) | [Phe-Asp + H]$^+$ (m/z 295.3) 10081 | [PheAsp + Na]$^+$ (m/z 317.2) 1033 | [PheAsp – Asp]$^+$ (m/z 148.1) 1370 | [Asp + H]$^+$ (m/z 134.2) 1930 | |

Accordingly, this invention develops a three-dimensional HPLC system with an ion trap mass spectrometer, for determining amino acid sequence of a protein or a polypeptide. The principle described in the above examples can apply to any other proteins or polypeptides.

The detection limit of the fluorescence detector 22 used in the system is about 0.1-0.2 µg mL$^{-1}$ with the relative standard deviation (RSD) about 1.6-6.5%, and the detection limit of the mass spectrometer 24 is about 0.9-1.1 µg mL$^{-1}$ with RSD about 17.3-23.7%, revealing excellent sensitivity and accuracy.

The determination procedure of the present invention is a "small-to-large" procedure. The constituent amino acids are firstly confirmed, then constructing any possible dipeptides by the constituent amino acids and confirming them by the molecular weight signal (m/z) of mass spectrometry. Continually, from the confirmed dipeptides, possible larger peptides of tripeptide, tetrapeptide, pentapeptide and so on, in an order from small molecular weight to large molecular weight, are constructed and confirmed by matching the molecular weight signal (m/z) of mass spectrometry. In addition, because the enantiomers of amino acids and amino acid isomers can be separated by the second column 12, the determined sequence can be 100% accurate. Noticed that conventional art uses "large-to-small" determination procedure, which is different from that of the present invention. In addition, a database is unnecessary for the determination procedure of the present invention, and the procedure can be assisted by a computer. Accordingly, the present invention provides systems and methods for determining the amino acid sequence of a protein or polypeptide in an effective and fast manner.

Although specific embodiments have been illustrated and described, it will be appreciated by those skilled in the art that various modifications may be made without departing from the scope of the present invention, which is intended to be limited solely by the appended claims.

What is claimed is:

1. A system for determining the amino acid sequence of a protein or a polypeptide, comprising:
   a reactor controlled at a predetermined temperature to thermally hydrolyze the polypeptide or the protein to a hydrolyte solution comprising amino acids and their enantiomers, short peptides formed by the amino acids and their enantiomers, and un-hydrolyzed polypeptide or un-hydrolyzed protein;
   a first liquid chromatography column connecting to an ultraviolet detector so as to separate the amino acids and their enantiomers, short peptides, and un-hydrolyzed polypeptide or un-hydrolyzed protein;
   a second liquid chromatography column connecting to a fluorescence detector so as to identify the amino acids and their enantiomers;
   a third liquid chromatography column connecting to a mass spectrometer so as to identify the short peptides and un-hydrolyzed polypeptide or un-hydrolyzed protein and obtain a molecular weight signal (m/z) of mass spectrometry, wherein the mass spectrometer is an ion-trap mass spectrometer with an Electrospray Ionization Interface (ESI), and the first liquid chromatography column, the second liquid chromatography column, and the third liquid chromatography column are initially online parallel connected by a first column switching valve and a second column switching valve, so that the first liquid chromatography column, the second liquid chromatography column, and the third liquid chromatography column are initially run independently;
   the first column switching valve receiving the separated hydrolyte solution eluted out of the first liquid chromatography column and being switched to connect the first liquid chromatography column and the second liquid chromatography column in series, such that the amino acids and their enantiomers of the hydrolyte solution flow into the second liquid chromatography column for analysis, and the first column switching valve is switched back when the amino acids and their enantiomers completely flow into the second liquid chromatography column; the second column switching valve comprising a sampling loop and being switched when the short peptides of the hydrolyte solution are eluted out from the first liquid chromatography column such that the short peptides of the hydrolyte solution flow into the sampling loop;
   a third column switching valve connected with the third liquid chromatography column, wherein the second column switching valve and the third column switching valve are simultaneously switched such that the short peptides in the sampling loop flow into the third liquid chromatography column to separate copper ions in a mobile phase for the first liquid chromatography column and the second liquid chromatography column from the short peptides, such that copper ions flow to a waste collector;
   an injection syringe continually injecting a solvent to the mass spectrometer as the copper ions flowing to the waste collector for a period of time, wherein the third column switching valve is switched after the copper ions are eluted, so that the third liquid chromatography column and the mass spectrometer are connected in series and the short peptides out from the third liquid chromatography column are analyzed by the mass spectrometry for their corresponding m/z; and a computer program to assist the amino acid sequencing procedure by implementing a method comprising the steps of:

constructing one or more possible short peptides from the identified amino acid enantiomers by the second liquid chromatography column; and confirming the one or more possible short peptides by matching the molecular weight obtained from the molecular weight signal (m/z) of mass spectrometry in an order from small molecular weight to large molecular weight, so as to determine the amino acid sequence of the polypeptide or the protein.

2. The system as recited in claim 1, wherein the first liquid chromatography column is an affinity chiral chromatography column using copper sulphate/methanol solution as its mobile phase.

3. The system as recited in claim 1, wherein the second liquid chromatography column is a ligand-exchange chromatography column using copper sulphate/methanol solution as its mobile phase.

4. The system as recited in claim 3, wherein the volume ratio of copper sulphate- to-methanol is 90/10.

5. The system as recited in claim 1, wherein the third liquid chromatography column is a reversed-phase chromatography column using 100% methanol as its mobile phase.

\* \* \* \* \*